United States Patent [19]
Wienand et al.

[11] Patent Number: 6,085,575
[45] Date of Patent: Jul. 11, 2000

[54] PROCESS FOR THE DETERMINATION OF THE EXHAUST GAS TEMPERATURE AND OF THE AIR/FUEL RATIO LAMBDA AND A SENSOR ARRANGEMENT FOR EXECUTION OF THE PROCESS

[75] Inventors: Karlheinz Wienand, Aschaffenburg; Edelbert Hafele, Karlsruhe, both of Germany

[73] Assignee: Heraeus Electro-Nite International N.V., Belgium

[21] Appl. No.: 09/162,183

[22] Filed: Sep. 28, 1998

[30] Foreign Application Priority Data

Oct. 10, 1997 [DE] Germany .............. 197 44 672
Feb. 14, 1998 [DE] Germany .............. 198 06 110

[51] Int. Cl.[7] ............... G01N 7/00; F02D 41/00; H01M 8/10
[52] U.S. Cl. .............. 73/23.32; 123/697; 429/33
[58] Field of Search ............... 73/23.31, 23.32, 73/31.06; 60/276, 284; 123/687, 697; 204/408; 429/33

[56] References Cited

U.S. PATENT DOCUMENTS

| | | |
|---|---|---|
| 4,007,435 | 2/1977 | Tien . |
| 4,407,704 | 10/1983 | Mase et al. . |
| 4,453,397 | 6/1984 | Ohta et al. ............ 73/23.31 |
| 4,732,128 | 3/1988 | Yoshioka et al. ...... 73/23.31 |
| 5,435,172 | 7/1995 | Pelters et al. . |
| 5,696,313 | 12/1997 | Hafele .................. 73/23.31 |

FOREIGN PATENT DOCUMENTS

| | | |
|---|---|---|
| 0 001 512 A1 | 4/1979 | European Pat. Off. . |
| 0 040 662 A1 | 12/1981 | European Pat. Off. . |
| 0 056 752 A1 | 7/1982 | European Pat. Off. . |
| 0 563 613 A2 | 10/1993 | European Pat. Off. . |
| 0 723 071 A1 | 7/1996 | European Pat. Off. . |
| 37 20 097 A1 | 1/1988 | Germany . |
| 38 35 852 A1 | 4/1990 | Germany . |
| 43 20 881 A1 | 9/1994 | Germany . |
| 43 39 692 A1 | 5/1995 | Germany . |
| 1 423 641 | 2/1976 | United Kingdom . |

*Primary Examiner*—Hezron Williams
*Assistant Examiner*—Jay L. Politzer
*Attorney, Agent, or Firm*—George H. Gerstman; Garrettson Ellis

[57] ABSTRACT

According to the state of the art, either two separate sensor elements are generally used to determine the exhaust gas temperature and the air/fuel ratio, lambda, or the temperature and lambda readings are not taken simultaneously, at least at temperatures of less than 250° C. In addition, sufficiently precise simultaneous measurement is only possible during stationary operation. The process according to the invention and the corresponding sensor arrangement now make it possible to obtain a precise temperature and lambda reading at a minimal degree of metrological complexity, especially under non-stationary conditions, in that a heated sensor, which exhibits a temperature-sensitive and oxygen-sensitive element on a carrier element, is used to measure the exhaust gas temperature, even at low temperatures with the heating system switched off, while a lambda reading is obtained simultaneously, with the latter being possible only at higher temperature ranges.

5 Claims, 1 Drawing Sheet

PROCESS FOR THE DETERMINATION OF THE EXHAUST GAS TEMPERATURE AND OF THE AIR/FUEL RATIO LAMBDA AND A SENSOR ARRANGEMENT FOR EXECUTION OF THE PROCESS

FIELD OF THE INVENTION

The invention relates to a process for the determination of the exhaust gas temperature and of the air/fuel ratio lambda, a sensor arrangement for execution of the process and the application of the sensor arrangement.

BACKGROUND OF THE INVENTION

A process for determining the exhaust gas temperature is known from DE 38 35 852 A1, whereby the internal resistance of a lambda sensor positioned in the exhaust gas is measured. Under stationary conditions, the exhaust gas temperature ($T_a$) can be inferred on the basis of our knowledge of the relationships between internal resistance ($R_i$) and probe temperature ($T_s$). DE 38 35 852 A1 provides additional options to account for the effects of the composition of the mixture on the accuracy of the temperature reading. The process which is known as a result of this state of the art operates at a degree of precision of 0.5 per cent. According to DE 38 35 852 A1, a multitude of internal resistance temperature characteristic curves, each for a different lambda value, is needed to achieve more precise readings. Furthermore, the operating conditions are factored into the arithmetic relationship between $T_s$ and $T_a$.

DE 43 39 692 A1 discloses a generic process for determining the exhaust temperature by means of an electrically heated lambda probe, where the exhaust gas temperature is inferred by the amount of electrical power needed to keep the lambda probe at a constant temperature. In this process, the exhaust gas temperature can be determined directly if the flow of exhaust gas remains virtually constant. However, if the exhaust gas flow rate changes together with the operating condition of the combustion system, a characteristic curve must be plotted for each individual operating condition, with the composite view of these curves producing a characteristic diagram. Other parameters that influence the operating condition and, consequently, the measuring inaccuracy of the sensors, must also be taken into account when determining the exhaust gas temperature. For example, because of the relationship between engine speed and exhaust gas flow rate, a characteristic diagram involving electric output and engine speed must also be used to determine the exhaust gas temperature. Other possible parameters include the throttle angle or the manifold pressure. Given the multitude of possible influencing parameters, this process cannot be expected to deliver a substantial degree of accuracy.

The combination of a heated lambda probe with variable sensor characteristics and an additional lambda probe with constant characteristics is described in DE 43 20 881. Because of the spatial proximity of the two sensor elements, the constant signal can be calibrated by means of the variable signal, provided the probe temperature is known. The additional electron-conducting temperature sensor is used to measure the probe temperature, so that a constant temperature level can be maintained. The calculation of the exhaust gas temperature, as described in the processes according to DE 38 35 852 A1 and DE 43 39 692 A1, is not described here. The temperature-sensitive element considered in DE 38 35 852 A1 and DE 43 39 692 A1 is the internal resistance of the ion-conducting electrolytes. However, the internal resistance of the electrolytes only enters the range of measurable resistance at higher temperatures. Testing of exhaust gas in the range of 0 to 250° C. is not possible.

Due to polarization phenomena, the measurement of internal resistance is associated with substantial metrological complexity. The lambda probes described there are highly unfavorable in terms of their geometry. Because of the low immersion depth of the tailpipe, only peripheral flow is measured and the reading is heavily falsified by the temperature of the tailpipe.

The objective of this invention is to provide a process and a suitable sensor arrangement for the determination of the exhaust gas temperature and of lambda that permits a precise temperature measurement across the entire temperature range and under various operating conditions, especially in non-stationary cases, and with minimal metrological complexity.

BRIEF SUMMARY OF THE INVENTION

In accordance with the present invention, a heatable sensor, with its temperature-sensitive and oxygen-sensitive element, is immersed into at least 20% of the depth of a catalytic converter body or of a tailpipe at a point after the catalytic converter, and where, with the heat switched off and only at exhaust temperatures greater than 250° C., the exhaust gas temperature reading is taken simultaneously with the oxygen reading and/or with the determination of lambda.

Lambda is advantageously determined by means of a potentiometric (without voltage source), amperometric or resistive measuring process.

In terms of the sensor arrangement, it has proven to be advantageous to apply the temperature-sensitive element and the oxygen-sensitive element, using thin-layer or thick-layer technology, to an electrically insulating carrier, such as aluminum oxide, or to an electrically insulating layer, with the temperature-sensitive element being made of an electron-conducting or semiconducting material.

A platinum group metal, especially platinum or a platinum alloy, is used as the electron-conducting material. Depending on the specific execution, a platinum resistor element with PTC characteristics (positive temperature coefficient) or, for example, a Pt/PtRh thermoelement, may be advantageous.

Alternatively, the use of aluminum oxide-based, chromium oxide-based and/or iron oxide-based semiconducting thermistors that exhibit NTC characteristics (negative temperature coefficient) has also proven to be advantageous.

$ZrO_2$ has proved to be effective as the material used in the oxygen-sensitive element, provided the potentiometric or amperometric principle of measurement is applied. Perovskitic semiconductor materials, especially titanates, should be used in resistive sensors.

The process of this invention is especially suitable for checking the operativeness of a catalytic converter in that, for example, the thermal toning that takes place during catalytic conversion of the exhaust gas components is detected by the temperature sensor and the intensity of this thermal toning represents a measure of the rate of conversion of the catalytic converter. Furthermore, the measured exhaust gas temperature and/or the measured lambda value can be compared with a temperature or lambda value of another temperature or lambda sensor installed in the exhaust gas flow and/or be used for its calibration. Specifically, the sensor arrangement according to the invention is used to perform, as a comparison measurement, the calibration of a first lambda sensor with a second lambda sensor under hot operating conditions (warmed-up engine), the so-called onboard diagnosis of catalytic converter operation through measurement of the temperature difference between two temperature sensors (during hot operation), and the calibration of two temperature sensors at room temperature (calibration to the same temperature).

The sensor of this invention preferably has a temperature-sensitive element with an electron-conducting material which preferably comprises a resistor element with PTC characteristics or a thermoelement. The electron conducting material may comprise a platinum group metal such as platinum or a platinum alloy. Also, the temperature-sensing element may comprise a semiconducting material, and optionally further comprising a thermistor. Such thermistors may comprise a ceramic material with NTC characteristics. The ceramic material may comprise a metal oxide such as aluminum oxide, chromium oxide, or iron oxide. Also, the temperature sensing element may be applied, using thin-layer or thick-layer technology, to the electrically insulating carrier or the electrically insulating layer.

The oxygen-sensitive element may comprise a material consisting primarily of $ZrO_2$, and operates according to potentiometric or amperometric principles of measurement. The oxygen-sensitive element may comprise a Perovskitic semiconductor material, and may operate according to a resistive principle of measurement. Such a semiconductor material may comprise a titanate.

A more detailed explanation of the invention is provided in the following description and claims and is illustrated in the accompanying drawings.

DETAILED DESCRIPTION OF THE ILLUSTRATIVE EMBODIMENT

Figure 1:
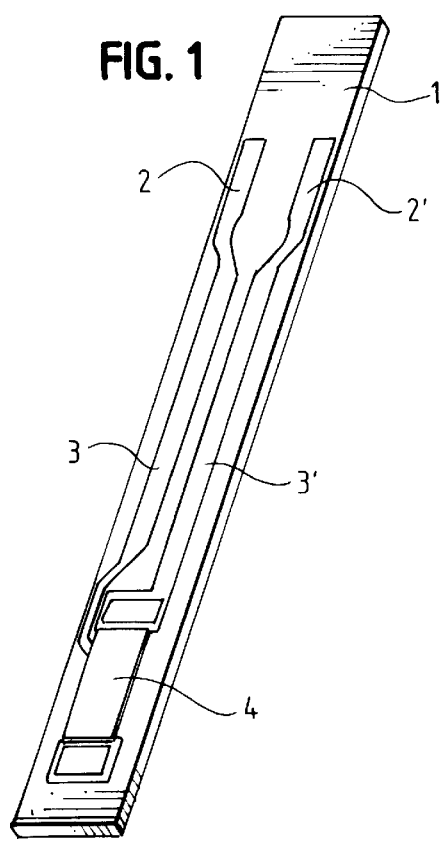
FIG. 1 is a front perspective view of a sensor constructed in accordance with the principles of the present invention.

FIG. 1 depicts the front side of a carrier element 1 made of $Al_2O_3$ and shaped as a flat rod, with two contact pads 2, 2' arranged on its one end. A lead 3, 3' runs from each of these contact pads 2, 2' to the other end of the carrier element, where a precision resistor is attached and contacted with the leads 3, 3'. A Pt 200 resistor used as a precision resistor serves here as a temperature-sensitive element 4.

Figure 2:
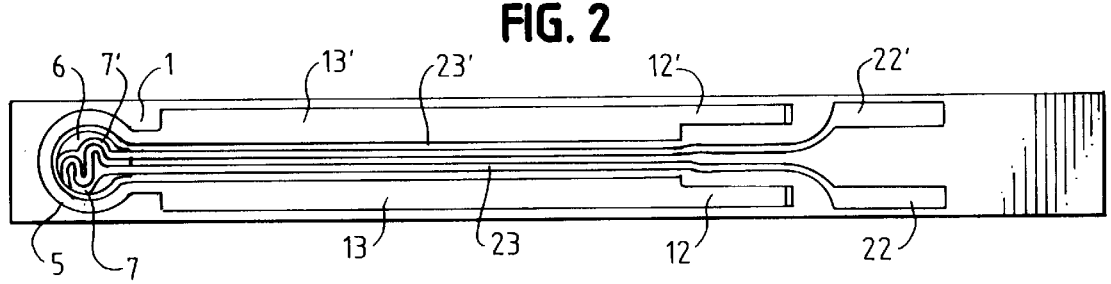
FIG. 2 is a back plain view of the sensor of FIG. 1.

FIG. 2 depicts the back side of the carrier element 1, to which are applied a heating element 5 with corresponding leads 13, 13', the contact pads 12, 12', and an oxygen-sensitive element 6 consisting of a layer made of $SrTiO_3$. Two electrodes 7, 7' containing precious metal, whose leads 23, 23' lead to the contact pads 22, 22', are arranged on the oxygen-sensitive element 8, which is designed as a layer.

Together with the two electrodes 7, 7', the layer 6 represents a resistive lambda sensor. The exhaust gas temperature and the partial oxygen pressure in the exhaust gas can be measured with the sensor arrangement according to FIGS. 1 and 2.

Figure 3:
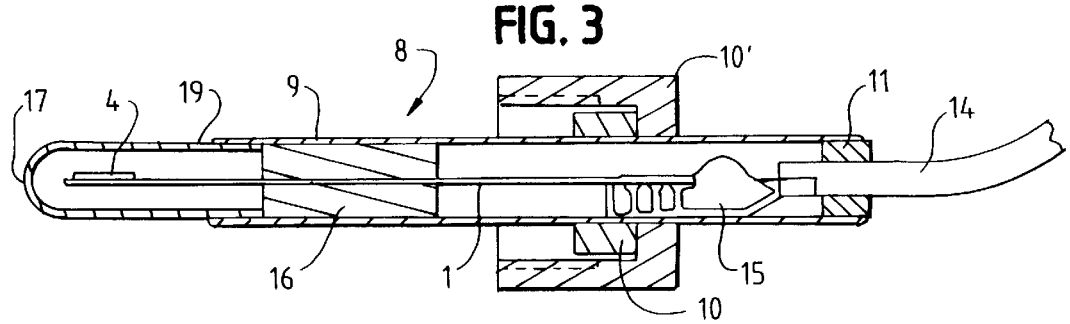
FIG. 3 is a cross-sectional view of a sensor casing with the sensor arrangement according to FIGS. 1 and 2.

FIG. 3 depicts a cross-section of a sensor casing 8 that encloses the sensor arrangement according to the invention on the carrier element 1. The casing 8 encompasses a metal protective tube 9 with a protective cap 19 that is immersed into the gas being tested, a limit strip 10 for an overflow nut 10', a gasket 11, a cable connection 14, contact clip 15 and a high temperature-resistant cushioning pad 16 inside the protective tube 9 to support the carrier element 1. The protective cap 19 exhibits at least one gas inflow opening 17 which, in this case, consists of a hole in the tip of the protective cap 19. Installation into this type of casing has proved to be especially effective when using the sensor arrangement in a process for exhaust gas testing in motor vehicle exhaust gas systems.

Although an illustrative embodiment of the invention has been shown and described, it is to be understood that various modifications and substitutions may be made by those skilled in the art without departing from the novel spirit and scope of the present invention.

What is claimed is:

1. A process for determining the exhaust gas temperature and the air/fuel ratio of an exhaust gas including the steps of providing a sensor with a heating system, a temperature-sensitive element, and an oxygen-sensitive element on an electrically insulating carrier or an electrically insulating layer; and measuring the exhaust gas temperature and the air/fuel ratio simultaneously where, at temperatures below 250 degrees C., the temperature of the exhaust gas is determined by the temperature sensitive element, the heating system is turned off, and the oxygen-sensitive element does not determine the air/fuel ratio; and, at temperatures above 250 degrees C., the heating system heats the sensor, the temperature sensitive element determines the temperature, the determined temperature is used to control the heating element, and the oxygen-sensitive element determines the air/fuel ratio.

2. The process of claim 1 wherein the method for determination of the air/fuel ratio is selected from the group consisting of resistive, potentiometric and amperometric methods of measurement.

3. The process of claim 1 further comprising monitoring the operativeness of a catalytic converter.

4. The process of claim 1 further comprising calibrating additional sensors in a flow of exhaust gas with the same composition.

5. The process of claim 1 in which said sensor is immersed into at least twenty percent of the depth of a catalytic converter body or of a tailpipe at a point after the catalytic converter.

* * * * *